United States Patent [19]

Schmidt-Dunker et al.

[11] 4,104,366
[45] Aug. 1, 1978

[54] COMPOSITIONS FOR PREPARATION OF AQUEOUS SOLUTIONS OF LOW VALENCE $^{99}$TECHNITIUM SALTS

[75] Inventors: Manfred Schmidt-Dunker; Wolfgang Greb, both of Düsseldorf, Fed. Rep. of Germany

[73] Assignee: Henkel Kommanditgesellschaft auf Aktien, Dusseldorf-Holthausen, Fed. Rep. of Germany

[21] Appl. No.: 725,883

[22] Filed: Sep. 23, 1976

[30] Foreign Application Priority Data

Sep. 29, 1975 [DE] Fed. Rep. of Germany ....... 2543349

[51] Int. Cl.$^2$ ...................... A61K 29/00; A61K 43/00
[52] U.S. Cl. .................. 424/1; 260/502.4 P; 260/502.5; 424/9
[58] Field of Search .................. 260/502.4 R, 502.4 P, 260/502.5; 424/1, 1.5, 9

[56] References Cited

U.S. PATENT DOCUMENTS

| | | |
|---|---|---|
| 3,851,044 | 11/1974 | Adler et al. ............ 424/1 X |
| 3,965,254 | 6/1976 | Tofe et al. ................ 424/1 |
| 3,974,268 | 8/1976 | Subramanian et al. ........ 424/1 |
| 3,976,762 | 8/1976 | Köhler et al. ............. 424/1 |
| 3,983,227 | 9/1976 | Tofe et al. ............... 424/1 |
| 3,989,730 | 11/1976 | Subramanian et al. ........ 424/1 |

*Primary Examiner*—Benjamin R. Padgett
*Assistant Examiner*—Christine M. Nucker
*Attorney, Agent, or Firm*—Hammond & Littell

[57] ABSTRACT

Aqueous solutions of $^{99}$technetium salts wherein the $^{99}$technetium is in reduced valencey state, when administered to mammals, permit identification of the skeleton and of calcareous tumors by scintigraphy (radiographic scanning). The solutions are conveniently prepared by mixing one or more phosphonic acids (or their salts) with one or more reducing salts, and adding the mixture to an aqueous solution of a pharmaceutically acceptable $^{99}$pertechnetate salt. Reduction of the valence of the technetium occurs rapidly, and the resulting solution is adequately stable for use in scintigraphy.

The phosphonic acid and reducing salt components can be premixed. Aqueous solutions of the premix are stable for long periods of time in the absence of free oxygen and the premix is stable to air so long as it is dry.

12 Claims, No Drawings

COMPOSITIONS FOR PREPARATION OF AQUEOUS SOLUTIONS OF LOW VALENCE $^{99}$TECHNITIUM SALTS

The present invention relates to water-soluble compositions or complexes of certain water-soluble phosphonic acids and salts with certain water-soluble polyvalent metal salts, for use in the preparation of stable aqueous solutions containing radioactive $^{99m}$ technetium.

The invention includes the compositions of the phosphonic-polyvalent metal components in tableted dry mix and in aqueous solution forms. The invention also includes aqueous solutions of low valence $^{99m}$ technetium compounds having a content of said phosphonic-polyvalent metal compositions as stabilizer, and methods for the preparation of said solutions.

It has been known for some time that X-ray investigations for recognizing skeletal diseases and tumors, especially in the early stages, are not entirely satisfactory, even when effective treatment is possible. Newer methods have therefore been developed in which the radioactive isotopes fluorine-18 and strontium-85 are used, which are selectively adsorbed in the skeleton and in particular by diseased portions of the skeleton. These radioactive isotopes concentrate even in calcareous tumors. Bone or tissue diseases can then be recognized and their sites identified by radiography. The production of $^{18}$F, however, requires complex apparatus which is usually not present in hospitals, and in addition $^{18}$F has an extremely short half-life (only 110 minutes). The isotope $^{85}$Sr, on the other hand, has a very long half-life (65 days), but this isotope requires very long scanning periods because of its slow rate of decomposition and consequent low radio-emission rate.

Because of these disadvantages, interest has recently been directed to the radio isotope technetium-99$^m$, which has a half-life of 6 hours. Very convenient apparatus is available for its production, by which the isotope is obtained in the form of sodium $^{99m}$ pertechnetate by extraction with isotonic sodium chloride solution. In this form the technetium has a valence of 7.

The pertechnetate-99m ion differs from ions containing $^{18}$F and from $^{85}$Sr$^{2+}$ in that in the body, the pertechnetate ion is not specially bound in the skeleton or to calcareous tumors. It is therefore not practically useful for the scintographic examination of bones and calcareous tumors. In order to use it, therefore, the pertechnetium in the ion must be reduced to a relatively low oxidation state (i.e., to a low valence state) and then stabilized with a suitable complex former in this oxidation state. The valence of the technetium in this reduced state is 4. The complex former must also have a high selectivity for preferred adsorption by the skeleton or by calcareous tumors. Initial successes were achieved with certain polyphosphates whose complexes, however, have only moderate stability with low oxidation state technetium. A suitable complex was produced by mixing $^{99m}$ pertechnetate solution with an aqueous solution of ditin (II) ethane-1-hydroxy-1,1-diphosphonate (described in J. Nucl. Med. 13, 947 and 14, 73). The stability of this ditin (II) ethane-1-hydroxy-1,1-diphosphonate solution was restricted, however, with an excess of ethane-1-hydroxy-1,1-diphosphonate, especially since the tin (II) ion has a tendency to hydrolyze. A composition for the preparation of a material for the scintographic scanning of bones on this basis is described in German Patent No. 2,424,496.

It has now been found that certain aminophosphonic and amidophosphonic acids and their salts are very desirable complexing agents because of the high stability of their complexes with low oxidation state technetium ions and because of the high selectivity with which the $^{99m}$Tc deposits itself in the bone tissue or in calcareous tumors.

The object of producing a soluble-stable composition which on addition to aqueous pertechnetate salt solutions provides a stable, effective and selective form of $^{99}$ technetium suitable for the radiography of bones and calcareous tumors, is attained by preparations which contain a mixture of:

(A) at least one phosphonic compound of the theoretical formulae:

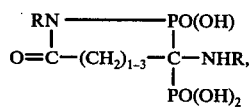

wherein R represents a substituent selected from group consisting of H and $C_{1-6}$ alkyl;

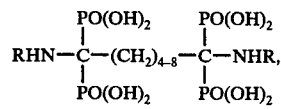

wherein R represents a substituent selected from the group consisting of H and $C_{1-4}$ alkyl;

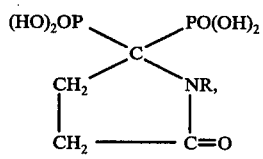

wherein R represents a substituent selected from the group consisting of H and $C_{1-6}$ alkyl;

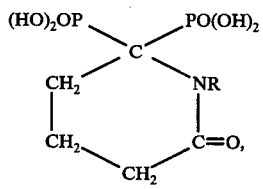

wherein R represents a substituent selected from the group consisting of H and $C_{1-6}$ alkyl;

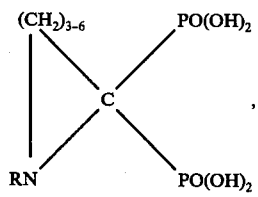

wherein R represents a substituent selected from the group consisting of H and $C_{1-4}$ alkyl;

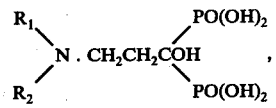

wherein $R_1$ and $R_2$ each represent a substituent selected from the group consisting of H and $C_{1-3}$ alkyl;

VII the pharmaceutically-acceptable water-soluble salts of phosphonic acids (I) - (VI); and (B) at least one salt selected from the group consisting of the water-soluble pharmaceutically-acceptable tin (II), iron (II) and chromium (II) salts and mixtures thereof in less than stoichiometric quantity, relative to component (A).

More in detail, we have found that a stable aqueous solution of a physiologically acceptable water-soluble salt of $^{99}$technetium which is preferentially absorbed by bone and by calcareous tumors, is formed when to an aqueous solution of a $^{99}$pertechnetate salt is added a sufficient amount of a composition of a water-soluble phosphonic compound and a water-soluble reducing salt to reduce the technetium in said pertechnetate salt to a lower valence. The reduction in valence occurs rapidly, and the resulting solution, containing 1 to 20 mCi per ml of combined technetium is suitable for intravenous administration for the above purpose. The valence of the reduced technetium is 4.

According to the present invention in a suitable amount of $^{99m}$ technetium compound which is administered for radiographic purposes is in the range of 0.05 to 0.3 mCi per kilogram of body weight.

It is possible, with these components, to produce in simple fashion highly stable compositions which are suitable for distribution and storage in solid form as tablets or in the form of solutions in an ampoule. After being added to an aqueous solution of a pertechnetate salt, the resulting solution is a very effective agent for diagnosing bone tumors, local disorders in bone metabolism and calcareous tissue tumors by the radiation scanning method.

The above phosphonic compounds can be used in free acid form. However, they can also be used for pharmaceutical purposes in the form of their pharmacologically harmless salts such as their sodium, potassium, magnesium, zinc, and ammonium salts, as well as their substituted ammonium salts such as mono-, di- or triethanol ammonium salts. Moreover, the phosphonic acids can be used in the form of their partial salts (where only a portion of the acid protons is substituted by other cations) and in the form of their whole salts. The partial salts, which react substantially neutrally in aqueous solution (providing a pH in the range of 5–9 at 1% concentration) are preferred. Mixtures of the above-mentioned salts may also be used.

The cation of the pertechnetate salt can be any of the foregoing, so long as the compound as a whole is water-soluble.

Particularly good results in respect of the stabilization of $^{99m}$Tc ions in the complex, the avoidance of the formation of colloidal particles, and the selectivity of the deposit of $^{99m}$Tc in the skeleton or in calcareous tumors are obtained with the partial sodium salts of the following preferred amino- and amido phosphonic acids:

1. 2-Hydroxy-2,7-dioxo-3-amino-3-phosphono-1-aza-2-phosphacycloheptane, disodium salt.
2. Azacycloheptane-2,2-diphosphonic acid, disodium salt.
3. Amino-1-hydroxypropane-1,1-diphosphonic acid, disodium salt.

These preferred phosphonic acid partial salts are well absorbed by the skeleton and are only slightly absorbed by the soft tissues of mammals, except calcareous tumors by which they are well absorbed. They are predominantly suitable for identifying bone metastases of masto- or prostato-carcinomae.

Phosphonic acids of formula (I) can be produced by reacting short-chained substituted or unsubstituted dicarboxylic acid diamides, $\alpha,\omega$-dinitriles or an imide (for example, succinimide) with a phosphonylating agent, for example the phosphorus (III) halogenides or $H_3PO_3$, and subsequently effecting acid hydrolysis.

Diaminoalkane-tetraphosphonic acids of formula II can be produced by reacting long-chained substituted or unsubstituted dicarboxylic acid diamides or $\alpha,\omega$-dinitriles with phosphonylating agents for example phosphorus III halogenides or $H_3PO_3$, and subsequently effecting acid hydrolysis.

Pyrrolidone-5,5-diphosphonic acids of formula III are obtained preferably by strongly alkaline hydrolysis of aminophosphonic acids of formula I in which the $-(CH_2)_{1-3}$ group is the $-(CH_2)_2-$ group.

Piperidone-6,6-diphosphonic acids of formula IV may be obtained preferably by the strongly alkaline hydrolysis of aminophosphonic acids of formula I in which the $-(CH_2)_{1-3}-$ substituent is the $-(CH_2)_3-$ group.

Azacycloalkane-2,2-diphosphonic acids of formula V may be produced preferably by reacting lactams with phosphonylating agents, for example phosphorus III halogenides or $H_3PO_3$.

3-Amino-1-hydroxypropane-1,1-diphosphonic acids of formula VI can be produced by phosphylating $\beta$-alanine or $\beta$-alanine alkylated on the nitrogen atom with phosphorus III halogenides or $H_3PO_3$.

The above phosphonic acids can be converted into the desired water-soluble salts by complete or partial neutralization with an aqueous alkali metal alkali solution, for example sodium carbonate, or the other alkalis disclosed above.

As reducing agents, tin(II), iron (II) and chromium (II) salts with pharmaceutically acceptable anions can be employed. Chlorides and sulfates are preferred anions because of their universally acknowledged safety and particularly anhydrous tin (II) chloride is preferred because of its high reducing power and also because of the absence of water of crystallization.

The addition of reducing agent serves to reduce the $^{99m}$ pertechnetate extracted from a commercial $^{99m}$ pertechnetate generator. The resultant lower oxidation state $^{99m}$ Tc ion can then be complexed by one or more of the above phosphonic complex formers and introduced into the organism for absorption by the skeleton or by calcareous tumors.

Aqueous solutions of the above phosphonic acids and tin (II), iron (II) or chromium (II) salts have the undesirable property of oxidizing or hydrolyzing when stored over periods of time in contact with air. The behavior can be prevented by sealing the solution under nitrogen in ampoules or by preparing the composition of the invention in the form of dry tablets or dragees. The compositions of the invention may thus be treated and preserved in stable form; they are only added to the $^{99m}$ pertechnetate solution shortly before its intended use.

An excellent agent for bone and tumor radiography is thereby obtained which supplies superior scintillation images with minimal absorption of metal ions by structures in the body.

The required $^{99m}$Tc activity is extremely low with substantially 10 to 15 millicuries (mCi), and the quantity of tin (II) required for its reduction to a lower valent state is also extremely small. The amount of the reducing agent which is added is at least sufficient to reduce substantially all of the technetium in the pertechnetate ions to a lower valent state. The preferred quantity, however, is above the quantity stoichiometrically required for complete reduction of the technetium content of the $^{99m}$ pertechnetate ion. Together with the again substantially larger amount of the phosphonate a $^{99m}$Tc-Sn-phosphonate complex (the exact structure of which is not known) is formed which is stabilized by excess phosphonate.

Preferably the compositions of the invention contain the reducing agent in amounts of 1 to 5% based on the weight of the phosphonate components present. It is added at least in sufficient amount to reduce substantially all of the technetium ions in the pertechnetate compound to a lower valence state and is preferably added in excess thereover.

It is advantageous for pharmaceutically-compatible fillers, such as glucose or sodium chloride, to be present as agents facilitating the handling and measuring of small quantities of the reducing complex-forming composition. Sodium chloride is preferred for this purpose, since it helps to maintain the isotonia even when the pertechnetate solution is diluted with sterile water, as is necessary occasionally.

The active components of the composition are mixed until homogeneous and the mixture in dry particulate state is placed in standard glass ampoules, or the mixture is compressed to form tablets when it contains glucose, sodium chloride, etc. as filler. However, it is preferable to produce a solution of the components which is put into standard ampoules in unit dose amount under nitrogen and lyophilized. The lyophilizate is stable under nitrogen or in a vacuum, that is, in the absence of free oxygen. An aqueous isotonic solution of the components can also be preserved by excluding free oxygen, e.g. by maintaining the solution under nitrogen. The solutions thus contain substantially no free oxygen.

The present invention will now be further described by the following examples. These examples illustrate preferred embodiments of the invention, and are not to be construed in limitation thereof.

A. COMPOSITIONS

EXAMPLE 1

An aqueous solution of 8 mg. of the disodium salt of 2-hydroxy-2,7-dioxo-3-amino-3-phosphono-1,2-azaphosphacycloheptane, 2 g. of water and 0.15 mg. of anhydrous tin (II) chloride is poured into a graduated 10 ml. standard ampoule. The solution is lyophilized and the ampoule is sealed under vacuum and stored.

For the purpose of use, the ampoule is opened and the mixture is dissolved in 5 ml. of sterile isotonic sodium $^{99m}$ pertechnetate solution and the resulting solution is injected intravenously into a mammal.

EXAMPLE 2

An aqueous solution of 8 mg. of the disodium salt of azacycloheptane-2,2-diphosphonic acid, 1 g. of water and 0.10 mg. of chromium (II) chloride is poured into a graduated standard glass ampoule. The solution is lyophilized and the ampoule is sealed under vacuum and stored. The ampoule is then opened, the substance within is dissolved in 5 ml. of sterile isotonic sodium chloride solution, and the resulting solution is injected after being mixed with the isotonic sodium $^{99m}$ pertechnetate solution.

EXAMPLE 3

8 mg. of the disodium salt 3-amino-1-hydroxypropane-1,1-diphosphonic acid and 0.15 mg. of iron (II) sulfate is finely ground dry state are poured into a graduated 5 ml. standard ampoule after which the ampoule is sealed under vacuum. For the purpose of use, the mixture is dissolved in 5 ml. of sterile isotonic sodium chloride solution and injected after being mixed with the isotonic sodium $^{99m}$ pertechnetate solution.

EXAMPLE 4

8 mg. of the disodium salt of 3-amino-1-hydroxypropane-1,1-diphosphonic acid and 0.15 mg. of tin (II) chloride, dissolved in 5 ml. of sterile isotonic sodium chloride solution, are poured into a graduated 10 ml. standard ampoule, which is processed as described in Example 1.

EXAMPLE 5

8 mg. of disodium salt of azacycloheptane-2,2-diphosphonic acid, 0.2 mg. of tin (II) chloride, 45 mg. of sodium chloride and 26.8 mg. of glucose are compressed to form mini-tablets weighing 80 mg. The tablets dissolve quickly in 5 ml. of sterile water and produce an isotonic solution.

EXAMPLE 6

4 mg. of the disodium salt of azacycloheptane-2,2-diphosphonic acid, 4 mg. of 3-amino-1-hydroxypropane-1,1-diphosphonic acid disodium salt, 0.2 mg. of iron (II) sulfate, 45 mg. of sodium chloride and 26.8 mg. of glucose are compressed to form mini-tablets weighing 80 mg. The tablets dissolve quickly in 5 ml. of sterile water and produce an isotonic solution.

EXAMPLE 7

8 mg. of the disodium salt of 2-hydroxy-2,7-dioxo-3-amino-3-phosphono-1,2-azaphosphacycloheptane disodium salt, 0.07 mg. of tin (II) chloride and 0.08 mg. of iron (II) sulfate, dissolved in 5 ml. of sterile isotonic sodium chloride solution, are put into a 5-ml. standard ampoule and processed as in Example 1.

EXAMPLE 8-9

The procedure of Examples 1 and 2 are repeated except that the ampoule is sealed with a content of dry nitrogen. Results are the same.

B. INJECTABLE SOLUTIONS

From each of these compositions, after the addition of substantially 5 ml. of sodium $^{99m}$ pertechnetate solution with an activity of substantially 50 mCi/ml. and after careful shaking at 20° C., an agent is obtained in dissolved form which can be dispensed to warm-blooded animals (i.e., mammals) by means of intravenous injection. In the case of human adults weighing about 70 kg, about 1 ml. of the solution is used for skeletal scintillography, the solution being injected slowly. In the case of children, correspondingly smaller quantities are used where necessary. Greater quantities may possibly be used for the scintillography of calcareous soft tissue, e.g. calcareous tumors or in the case of advanced calcification atherosclerosis. The injection is preferably made 1 to 2 hours after production.

C. SCINTILLOGRAPHY

Agents which were produced from the mixture according to Example 3 produced excellent results in skeletal scintillography. They proved particularly successful when looking for bone metastases in patients having mastocarcinoma or prostatocarcinoma and provide an ideal supplement to X-ray diagnostics.

Distribution studies in rats, which are a good model for the human being in these experiments, with activities of 0.01 to 1.0 mCi on $^{99m}$Tc, showed that in the case of the preferred compositions, substantially 60% to 70% of the dose typically passes to the skeleton. After three hours 5% of the active material can be found in the blood, the remainder being excreted with the urine. This distribution should be considered excellent.

The optimum time for scintillographical scanning is about 3 hours after injection. Other times are optimum after injection for the scintillography of calcareous soft tissue, such as tumors, muscular tissue or in the case of advanced calcification atherosclerosis. This time depends upon the regional blood clearance of the tissue concerned.

We claim:

1. A composition for use in the preparation of aqueous solution containing $^{99m}$technetium for use in the detection by scintography of bones and calcareous tumors, comprising:

(A) one or more water-soluble phosphonic compounds of the formulae:

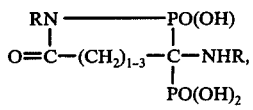

wherein R represents a substituent from the group consisting of H and $C_{1-6}$ alkyl;

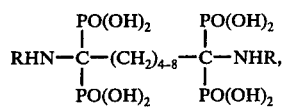

wherein R represents a substituent from the group consisting of H and $C_{1-4}$ alkyl;

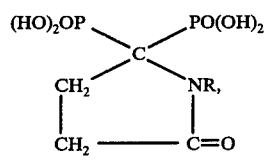

wherein R represents a substituent from the group consisting of H and $C_{1-6}$ alkyl;

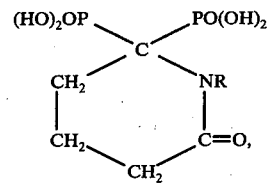

wherein R represents a substituent from the group consisting of H and $C_{1-6}$;

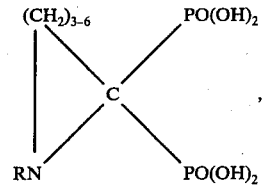

wherein R represents a substituent from the group consisting of H and $C_{1-4}$ alkyl;

VI the pharmaceutically-acceptable water-soluble salts of the above acids (I)—(V); and (B) a pharmaceutically acceptable water-soluble salt selected from the group consisting of tin (II), iron (II) and chromium (II) salts and mixtures thereof in less than stoichiometric quantity relative to component (A).

2. A composition according to claim 1, wherein the weight of component (B) is 1% to 5% of the weight of said component (A).

3. A composition according to claim 1 wherein the phosphonic compound is a partial salt.

4. A composition according to claim 1 in which component (A) contains a compound from the group consisting of the cyclic aminophosphonic acid of the formula

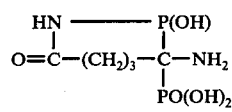

and a partial sodium salt thereof.

5. A composition according to claim 1 wherein component (A) contains a compound from the group consisting of azacycloheptane-2,2-diphosphonic acid and a partial sodium salt thereof.

6. A composition according to claim 1 wherein the component (B) is tin (II) chloride.

7. A composition according to claim 1 in dry mix tableted form.

8. A composition according to claim 1 in unit dosage form in an ampoule containing substantially no free oxygen.

9. A composition according to claim 1 in unit dosage form and in lyophilized state in an ampoule containing substantially no free oxygen.

10. A method of preparing a stable solution of a water-soluble salt of $^{99m}$technetium which is absorbed by bone and by calcareous tumors in mammals, which comprises adding to an aqueous solution of a $^{99m}$ pertechnetate salt a sufficient amount of a phosphonic acid-reducing agent composition according to claim 1 to reduce the technetium in said pertechnetate salt to a lower valency.

11. A method according to claim 10 wherein the said phosphonic acid reducing agent composition is added in dry tableted form.

12. A method according to claim 10 wherein the amount of said phosphonic acid reducing agent composition is added in excess of the amount which reduces substantially all of the technetium in said pertechnetate salt to a lower valence.

* * * * *